(12) United States Patent
Ummer et al.

(10) Patent No.: US 12,098,112 B1
(45) Date of Patent: *Sep. 24, 2024

(54) CARBON DIOXIDE REDUCTION METHOD WITH RED MUD CATALYST

(71) Applicant: KING FAHD UNIVERSITY OF PETROLEUM AND MINERALS, Dhahran (SA)

(72) Inventors: Aniz Chennampilly Ummer, Dhahran (SA); Galal Atef Ahmed Nasser, Dhahran (SA); Syed Ahmed Ali, Dhahran (SA); Mohammed Ahmed Yahya Sanhoob, Dhahran (SA); Akolade Idris Bakare, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/617,660

(22) Filed: Mar. 27, 2024

Related U.S. Application Data

(63) Continuation of application No. 18/183,821, filed on Mar. 14, 2023, now Pat. No. 11,981,615.

(51) Int. Cl.
*C07C 1/12* (2006.01)
*B01J 6/00* (2006.01)
(Continued)

(52) U.S. Cl.
CPC .............. *C07C 1/12* (2013.01); *B01J 6/001* (2013.01); *B01J 21/16* (2013.01); *B01J 35/612* (2024.01);
(Continued)

(58) Field of Classification Search
CPC ........ C07C 1/12; C07C 2521/16; B01J 6/001; B01J 21/16; B01J 35/1009; B01J 35/1014;
(Continued)

(56) References Cited

U.S. PATENT DOCUMENTS

| 10,537,872 B1 | 1/2020 | Saha |
| 2021/0229076 A1 | 7/2021 | Alsolami et al. |
| 2021/0268480 A1 | 9/2021 | Alsolami et al. |

FOREIGN PATENT DOCUMENTS

| CN | 110655342 A | 1/2020 |

OTHER PUBLICATIONS

Russkikh et al., "Turning Waste into Value: Potassium-Promoted Red Mud as an Effective Catalyst for the Hydrogenation of CO2", ChemSusChem, vol. 13, Issue 11, 2981-2987, 2020.
Xie et al.,"Electrochemical CO2 mineralization for red mud treatment driven by hydrogen-cycled membrane electrolysis", Chinese Journal of Chemical Engineering, vol. 43, 14-23, 2022.
Yoon et al., "Enhancement of syngas for H2 production via catalytic pyrolysis of orange peel using CO2 and bauxite residue", Applied Energy, vol. 254, 2019.

(Continued)

*Primary Examiner* — In Suk C Bullock
*Assistant Examiner* — Jason Y Chong
(74) *Attorney, Agent, or Firm* — Oblon, McClelland, Maier & Neustadt, L.L.P.

(57) ABSTRACT

A method for chemically reducing carbon dioxide ($CO_2$) with a red mud catalyst composition is provided includes introducing a gaseous mixture of $CO_2$ and $H_2$ into a reactor containing particles of the red mud catalyst composition. The method further includes reacting at least a portion of the $CO_2$ and $H_2$ in the gaseous mixture in the presence of the red mud catalyst composition at a temperature of 200 to 800° C., and under a pressure ranging from 5 to 100 bar to form a gaseous product including a chemical reduction product of the $CO_2$. A volume ratio of the $CO_2$ to the $H_2$ in the gaseous mixture is in a range of 1:10 to 10:1.

12 Claims, 5 Drawing Sheets

(51) Int. Cl.
    *B01J 21/16*       (2006.01)
    *B01J 35/61*       (2024.01)
    *B01J 35/63*       (2024.01)
    *B01J 37/00*       (2006.01)
    *B01J 37/02*       (2006.01)

(52) U.S. Cl.
    CPC ........... *B01J 35/613* (2024.01); *B01J 35/615* (2024.01); *B01J 35/633* (2024.01); *B01J 37/0009* (2013.01); *B01J 37/0201* (2013.01); *B01J 37/0203* (2013.01); *B01J 37/0236* (2013.01); *C07C 2521/16* (2013.01)

(58) Field of Classification Search
    CPC .......................... B01J 35/1019; B01J 35/1038; B01J 37/0009; B01J 37/0201; B01J 37/0203; B01J 37/0236
    See application file for complete search history.

(56) References Cited

OTHER PUBLICATIONS

Sushil et al. ("Catalytic applications of red mud, an aluminium industry waste: A review." Applied Catalysis B: Environmental 81 ( 2008) 64-77) (Year: 2008).

CARBON DIOXIDE REDUCTION METHOD WITH RED MUD CATALYST

CROSS-REFERENCE TO RELATED APPLICATIONS

The present application is a Continuation of U.S. application Ser. No. 18/183,821, now allowed, having a filing date of Mar. 14, 2023.

BACKGROUND

Technical Field

The present disclosure is directed to a method for carbon dioxide reduction, and particularly, to a method for chemically reducing carbon dioxide using red mud and modified red mud as catalyst.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The emission of greenhouse gases, such as carbon dioxide ($CO_2$), methane ($CH_4$), nitrous oxide ($N_2O$), and fluorinated gases, has become a major concern for energy sector industries across the globe. Efforts have been made to explore methods to minimize the emission of these gases into the atmosphere and improve the capture of such compounds. $CO_2$ is one of the most significant greenhouse gases, and it is crucial to capture and utilize it effectively, preferably at the source of its release. Conversion of $CO_2$ to value-added chemicals not only reduces $CO_2$ release into the atmosphere but also leads to economic benefits for investors. In the meanwhile, feasible catalytic processes can be developed to convert $CO_2$ into hydrocarbons, syngas, and oxygenates Lower olefins are the starting material for various plastics and polymers. Aromatics like benzene, toluene, and xylenes (BTX) are starting materials for many commodities and fine chemicals. Oxygenates like dimethyl ether and methanol also hold value in chemical industries. Syngas is widely used in industry as a source of energy and process raw material. Large-scale industries are seeking practical methods to add value to $CO_2$. Studies have been conducted to evaluate the effective utilization of different materials for catalytic applications, such as $CO_2$ valorization [Pawelec B, Guil-López R, Mota N, Fierro J L G, Navarro Yerga R M. Catalysts for the Conversion of CO(2) to Low Molecular Weight Olefins-A Review. Mater (Basel, Switzerland). 2021; 14(22)], ketonization [Weber J, Thompson A, Wilmoth J, Batra V S, Janulaitis N, Kastner J R. Effect of metal oxide redox state in red mud catalysts on ketonization of fast pyrolysis oil derived oxygenates. Appl Catal B Environ. 2019; 241:430-441], and adsorption [Wang S, Ang H M, Tadé M O. Novel applications of red mud as coagulant, adsorbent and catalyst for environmentally benign processes. Chemosphere. 2008; 72(11): 1621-1635]. $CO_2$ hydrogenation [Russkikh A, Shterk G, Al-Solami B H, Fadhel B A, Ramirez A, Gascon J. Turning Waste into Value: Potassium-Promoted Red Mud as an Effective Catalyst for the Hydrogenation of $CO_2$. ChemSusChem. 2020; 13(11):2981-2987] is also reported to be an effective process of converting $CO_2$ into hydrocarbons.

Although methods have been developed in the past for $CO_2$ reduction, there still exists a need to develop a simple and cost-effective method for converting $CO_2$ into valuable chemicals.

SUMMARY

In an exemplary embodiment, a method for chemically reducing carbon dioxide ($CO_2$) with a red mud catalyst composition is described. The method includes introducing a gaseous mixture of $CO_2$ and $H_2$ into a reactor containing particles of the red mud catalyst composition. The method further includes reacting at least a portion of the $CO_2$ and $H_2$ in the gaseous mixture in the presence of the red mud catalyst composition at a temperature of 200 to 800° C., and under a pressure ranging from 5 to 100 bar to form a gaseous product including a chemical reduction product of the $CO_2$. In some embodiments, a volume ratio of the $CO_2$ to the $H_2$ in the gaseous mixture is in a range of 1:10 to 10:1.

In some embodiments, the reactor is at least one selected from the group consisting of a fixed-bed reactor, a trickle-bed reactor, a moving bed reactor, a rotating bed reactor, a fluidized bed reactor, and a slurry reactor.

In some embodiments, the reactor is a fixed-bed reactor in the form of a cylindrical reactor which includes a top portion, a cylindrical body portion, a bottom portion, a housing. The housing has an open top and open bottom supportably maintained with the cylindrical body portion. The cylindrical reactor further includes at least one propeller agitator disposed in the bottom portion of the reactor. In some embodiments, the red mud catalyst composition is supportably retained within the housing, permitting fluid flow therethrough. In some embodiments, the bottom portion is cone-shaped or pyramidal. In some embodiments, a plurality of recirculation tubes fluidly connects the bottom portion of the cylindrical reactor with the cylindrical body portion of the cylindrical reactor.

In some embodiments, the volume ratio of the $CO_2$ to the $H_2$ is in a range of 1:1 to 1:5.

In some embodiments, the method includes reacting at least a portion of the $CO_2$ and $H_2$ in the gaseous mixture in the presence of the red mud catalyst composition at a temperature of 300 to 400° C., to form the gaseous product.

In some embodiments, the method includes reacting at least a portion of the $CO_2$ and $H_2$ in the gaseous mixture in the presence of the red mud catalyst composition under a pressure ranging from 30 to 40 bar to form the gaseous product.

In some embodiments, the method chemically reduces 10 to 25% of the $CO_2$ based on a total weight of the gaseous mixture.

In some embodiments, the red mud catalyst composition is a waste product from an aluminum extraction process.

In some embodiments, the red mud catalyst composition includes 5 to 20 wt. % Al, 2 to 28 wt. % Fe, 0.02 to 0.2 wt. % Mg, 2 to 10 wt. % Na, 0.02 to 0.2 wt. % P, 0.2 to 4 wt. % Ti, 0.02 to 0.2 wt. % V, 0.5 to 3 wt. % C, 0.05 to 0.2 wt. % S, and less than 0.01 wt. % Mn, each wt. % based on a total weight of the red mud catalyst composition by inductively coupled plasma optical emission spectroscopy (ICP-OES).

In some embodiments, the red mud catalyst composition includes particles having a specific surface area in a range of 5 to 120 square meter per gram ($m^2/g$).

In some embodiments, the red mud catalyst composition includes particles having a cumulative specific pore volume in a range of 0.01 to 0.1 cubic centimeter per gram ($cm^3/g$).

In some embodiments, the red mud catalyst composition has a hydrogen temperature-programmed reduction ($H_2$-TPR) of 0.5 to 5 millimoles per gram (mmol/g).

In some embodiments, the red mud catalyst composition has a temperature-programmed desorption of ammonia ($NH_3$-TPD) of 0.001 to 0.1 mmol/g. In some embodiments, the red mud catalyst composition has a temperature-programmed desorption of carbon dioxide ($CO_2$-TPD) of 0.01 to 0.5 mmol/g.

In some embodiments, the red mud catalyst composition is an alkali modified red mud catalyst composition or an alkaline modified red mud catalyst composition.

In some embodiments, the gaseous product includes methane, ethane, ethylene, propane, propylene, carbon monoxide, a hydrocarbon containing C4-C9, and aromatics. In some embodiments, the C4-C9 hydrocarbon comprises butane, butene, butyne, pentane, pentene, pentyne, hexane, hexene, hexyne, cyclohexane, cyclohexene, heptane, heptene, heptyne, octane, octene, octyne, nonane, nonene, and nonyne.

In some embodiments, the methane is present in the gaseous product at a concentration of 20 to 50 wt. %, and the carbon monoxide is present in the gaseous product at a concentration of 25 to 50 wt. %, each wt. % based on a total weight of the gaseous product.

In some embodiments, the method further includes preparing a modified red mud catalyst composition by pulverizing and calcining a red mud material at a temperature of at least 700° C. to form the red mud catalyst composition. The method of preparing a modified red mud catalyst composition further includes impregnating the red mud catalyst composition by soaking particles of the red mud catalyst composition in a salt solution and mixing to form the modified red mud catalyst composition as a crude mixture. Additionally, the method of preparing a modified red mud catalyst composition includes separating the modified red mud catalyst composition from the crude mixture, followed by drying, to obtain the modified red mud catalyst composition.

In some embodiments, the salt solution includes at least one salt selected from the group consisting of an alkali metal salt and an alkaline earth metal salt.

In some embodiments, the salt solution includes at least one salt selected from the group consisting of potassium fluoride (KF), potassium chloride (KCl), potassium bromide (KBr), potassium nitrate ($KNO_3$), potassium sulfate ($K_2SO_4$), potassium carbonate ($K_2CO_3$), potassium phosphate ($K_3PO_4$), and potassium hydroxide (KOH).

In some embodiments, the salt is present in the salt solution at a concentration of 0.5 to 10 wt. % based on a total weight of the salt solution.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
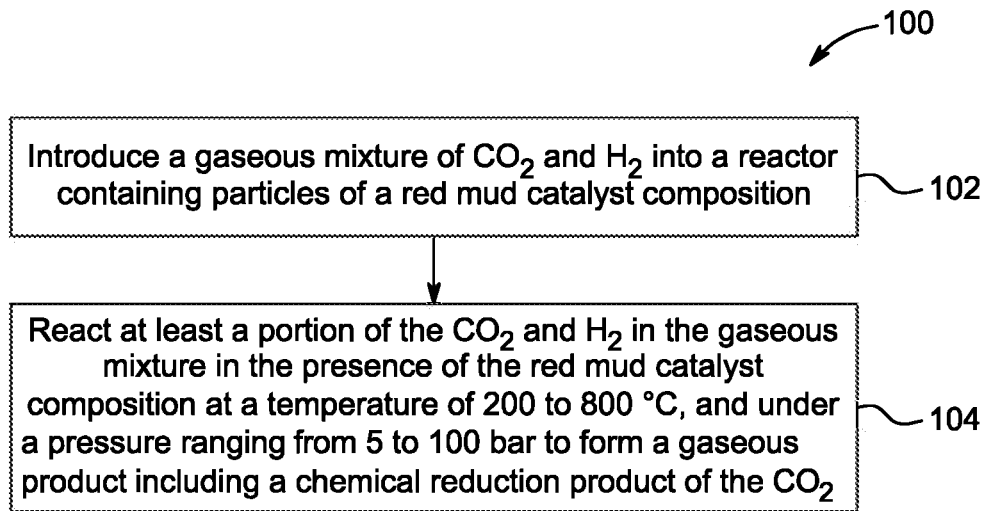
FIG. 1A is a method for chemically reducing $CO_2$ with a red mud catalyst composition, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed to a method for chemically reducing carbon dioxide ($CO_2$) with a red mud catalyst composition. The red mud catalyst composition, also referred to as composition, is used as a catalyst or a catalyst carrier for $CO_2$ hydrogenation reaction to produce valuable chemicals such as hydrocarbons and oxygenates.

Red mud is a caustic waste material of bauxite ore processing for the alumina extraction/aluminum refinement process (Bayer's process) and is utilized here as a catalyst for chemically reducing carbon dioxide ($CO_2$). Some of the sources of the red mud catalyst composition are the cement industries. Although the composition of the red mud may vary depending on the source, at a broad range, the red mud catalyst composition of the present disclosure has the following elemental composition as determined by ICP-OES.

In some embodiments, the red mud catalyst composition of the present disclosure includes 5 to 20 wt. %, preferably 2 to 19 wt. %, preferably 8 to 19 wt. %, and more preferably 9 to 19 wt. % of Al. In some embodiments, the red mud catalyst composition includes 2 to 28 wt. %, preferably 3 to 20 wt. %, preferably 3.5 to 19 wt. %, preferably 4 to 18 wt. %, preferably 4.5 to 16 wt. %, and more preferably 5 to 15 wt. % of Fe. In some further embodiments, the red mud catalyst composition includes 0.02 to 0.2 wt. %, preferably 0.05 to 0.2 wt. %, and more preferably 0.07 to 0.18 wt. % of Mg. In some preferred embodiments, the red mud catalyst composition includes 2 to 10 wt. % of Na, preferably 3 to 9 wt. %, preferably 3.5 to 8.5 wt. %, preferably 4 to 8 wt. %, and more preferably 4.4 to 7.7 wt. % of Na. In some more preferred embodiments, the red mud catalyst composition includes 0.02 to 0.2 wt. %, preferably 0.04 to 0.2 wt. %, and more preferably 0.05 to 0.2 wt. % of P. In some furthermore preferred embodiments, the red mud catalyst composition includes 0.2 to 4 wt. %, preferably 0.3 to 3.9 wt. %, preferably 0.4 to 3.88 wt. %, and more preferably 0.49 to 3.86 wt. % of Ti. In some preferred embodiments, the red mud catalyst composition includes 0.02 to 0.2 wt. %, preferably 0.03 to 0.18 wt. %, preferably 0.04 to 0.17 wt. %, and more preferably 0.05 to 0.16 wt. % of V. In some preferred embodiments, the red mud catalyst composition includes 0.5 to 3 wt. %, preferably 0.6 to 2.9 wt. %, preferably 0.7 to 2.8 wt. %, preferably 0.8 to 2.7 wt. %, and more preferably 0.98 to 2.57 wt. % of C. In some even more preferred embodiments, the red mud catalyst composition includes 0.05 to 0.2 wt. %, preferably 0.07 to 0.19 wt. %, preferably 0.09 to 0.18 wt. %, and more preferably 0.12 to 0.16 wt. % of S. In some even more preferred embodiments, the red mud catalyst composition includes less than 0.01 wt. % Mn, each wt. % based on a total weight of the red mud catalyst composition by ICP-OES. In some most preferred embodiments, Mn is preferably absent from or substantially absent from the red mud catalyst composition.

In one embodiment, the red mud catalyst composition contains 5 to 20 wt. % Al, 2 to 28 wt. % Fe, 0.02 to 0.2 wt. % Mg, 2 to 10 wt. % Na, 0.02 to 0.2 wt. % P, 0.2 to 4 wt. % Ti, 0.02 to 0.2 wt. % V, 0.5 to 3 wt. % C, 0.05 to 0.2 wt. % S, and less than 0.01 wt. % Mn, each wt. % based on the total weight of the red mud catalyst composition as determined by ICP-OES. In a further embodiment, the red mud catalyst composition contains about 9.83 wt. % Al, about 14.87 wt. % Fe, about 0.18 wt. % Mg, about 7.66 wt. % Na, about 0.19 wt. % P, about 3.86 wt. % Ti, about 0.16 wt. % V, about 0.98 wt. % C, about 0.16 wt. % S, each wt. % based on the total weight of the red mud catalyst composition as determined by ICP-OES. In yet a further embodiment, the red mud catalyst composition contains about 7.98 wt. % Al, about 23.88 wt. % Fe, about 0.13 wt. % Mg, about 6.56 wt. % Na, about 0.05 wt. % P, about 1.37 wt. % Ti, about 0.13 wt. % V, about 1.98 wt. % C, about 0.14 wt. % S, each wt. % based on the total weight of the red mud catalyst composition as determined by ICP-OES. In a still yet further embodiment, the red mud catalyst composition contains about 18.77 wt. % Al, about 4.98 wt. % Fe, about 0.07 wt. % Mg, about 4.47 wt. % Na, about 0.05 wt. % P, about 0.49 wt. % Ti, about 0.05 wt. % V, about 2.57 wt. % C, about 0.12 wt. % S, each wt. % based on the total weight of the red mud catalyst composition as determined by ICP-OES. Other ranges are also possible.

In some embodiments, the red mud catalyst composition may be used without any modifications. In some embodiments, the red mud catalyst composition may be used along with other conventionally used catalysts that are known in the art. In some embodiments, the red mud catalyst composition is an alkali-modified red mud catalyst composition (in other words—the red mud catalyst composition with an alkali metal such as (Li, Na, or K) or an alkaline-modified red mud catalyst composition (in other words—red mud catalyst composition modified with an alkaline earth metal—such as magnesium or calcium). In certain other embodiments, the red mud catalyst composition may be modified with transition metals such as, Ni, Ag, Mn, V, Pt, Pd, Fe, Mo, Co, Cu, Cr, and alloys thereof.

One of the key factors that affect the catalyst performance is the surface area. A higher surface area corresponds to greater sites for binding the reactant, and greater conversion. In some embodiments, the red mud catalyst composition includes particles having a specific surface area in a range of 5 to 120 m$^2$/g, preferably 10 to 100 m$^2$/g, preferably 15 to 80 m$^2$/g, and yet more preferably 16 to 58 m$^2$/g. Other ranges are also possible. As used herein, the term "specific surface area" refers to the property of solids defined as the total surface area of a material per unit of mass, or solid or bulk volume. The red mud catalyst composition includes particles having a cumulative specific pore volume in a range of 0.01 to 0.1 cm$^3$/g, preferably 0.02 to 0.08 cm$^3$/g, and yet more preferably 0.03 to 0.07 cm$^3$/g. Other ranges are also possible. As used herein, the term "pore volume" refers to the total volume of openings in a bed of adsorbent particles. In some embodiments, the red mud catalyst may be of any shapes and any configurations such as spherical, cubic, rod-shaped, irregular, fibrous, plate-like, and polyhedral. In some embodiments, binder materials such as alumina, silica, alumino silicates, clay, carboxy methyl cellulose, polyethylene glycol and a combination thereof may be added during the shaping step.

The crystalline structure of the red mud catalyst is characterized by X-ray diffraction (XRD). In some embodiments, the XRD patterns are collected in a Rigaku diffractometer (Miniflex) equipped with a Cu-Kα radiation source (λ=0.15406 nm) for a 2θ range extending between 10 and 80°, preferably 20 and 70°, further preferably 30 and 60° at an angular rate of 0.005 to 0.04° s$^{-1}$, preferably 0.01 to 0.03° s$^{-1}$, or even preferably 0.02° s$^{-1}$.

Figure 2:
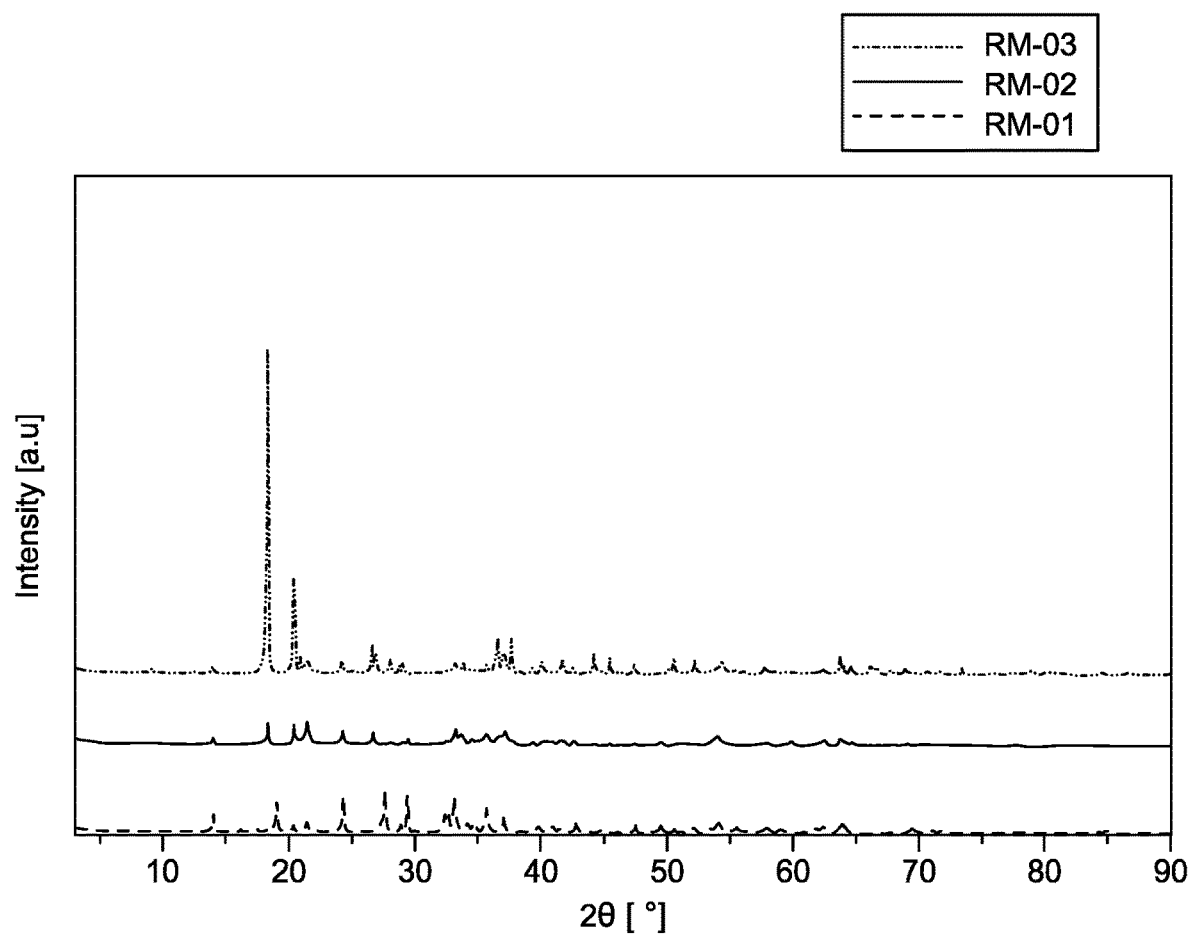
FIG. 2 depicts X-ray diffraction (XRD) patterns of red mud samples, RM-1, RM-2, and RM-3, according to certain embodiments.
Figure 3:
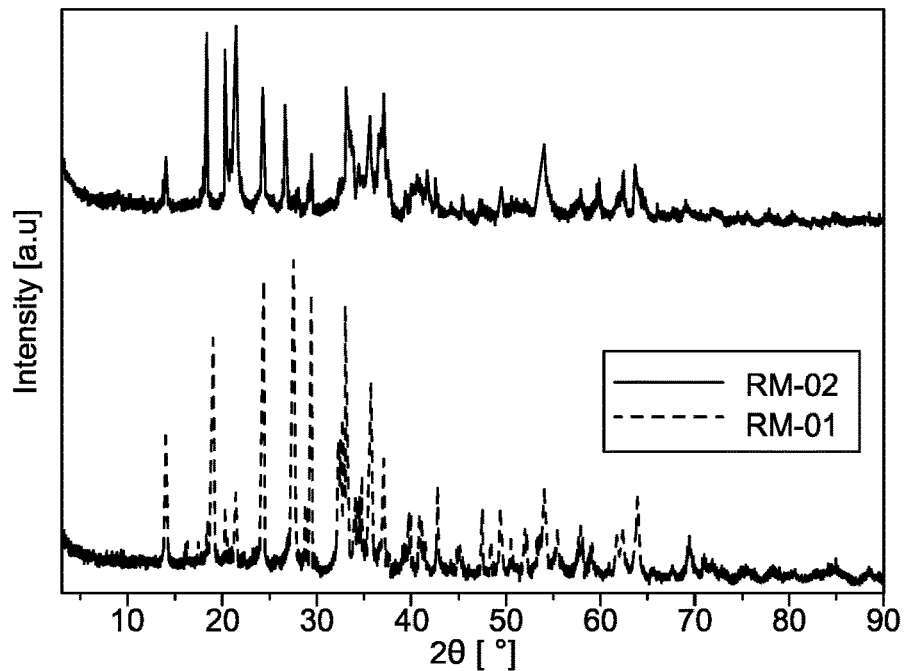
FIG. 3 depicts zoomed XRD patterns of the red mud samples of FIG. 2, according to certain embodiments.

FIG. 2 depicts X-ray diffraction (XRD) patterns of red mud samples, RM-1, RM-2, and RM-3. FIG. 3 depicts zoomed XRD patterns of the red mud samples of FIG. 2. In some embodiments, the red mud catalyst RM-1 has a first intense peak with a 2 theta (θ) value in a range of 12 to 15°, preferably about 13.8° in the XRD spectrum, a second intense peak with a 2θ value in a range of 18 to 20°, preferably about 18.5°, a third intense peak with a 2θ value in a range of 20 to 22°, preferably about 21.5°, a fourth intense peak with a 2θ value in a range of 23 to 25°, preferably about 24.5°, a fifth intense peak with a 2θ value in a range of 25 to 27.5°, preferably about 26°, a sixth intense peak with a 2θ value in a range of 27 to 30°, preferably about 29°, at least one seventh intense peak with a 2θ value in a range of 30 to 40°, preferably 32 to 38°, or even more preferably about 32 to 35°, at least one eighth intense peak with a 2θ value in a range of 40 to 45°, preferably 41 to 43°, or even more preferably about 42°, at least one ninth intense peak with a 2θ value in a range of 45 to 50°, preferably 47 to 49°, or even more preferably about 48°, at least one tenth intense peak with a 2θ value in a range of 50 to 60°, preferably 52 to 58°, or even more preferably about 54 to 56°, at least one eleventh intense peak with a 2θ value in a range of 60 to 65°, preferably 62 to 65°, or even more preferably about 63 to 65°, at least one twelfth intense peak with a 2θ value in a range of 65 to 80°, preferably 67 to 70°, or even more preferably about 68 to 69°, as depicted in FIGS. 2 and 3. Other ranges are also possible.

In some further embodiments, the red mud catalyst RM-2 has a first intense peak with a 2 theta (θ) value in a range of 12 to 15°, preferably about 13.8° in the XRD spectrum, a second intense peak with a 2θ value in a range of 18 to 20°, preferably about 18.2°, a third intense peak with a 2θ value in a range of 20 to 22°, preferably about 21°, a fourth intense peak with a 2θ value in a range of 23 to 25°, preferably about 24.5°, a fifth intense peak with a 2θ value in a range of 25 to 27.5°, preferably about 26°, a sixth intense peak with a 2θ value in a range of 27 to 30°, preferably about 28°, at least one seventh intense peak with a 2θ value in a range of 30 to 40°, preferably 32 to 38°, or even more preferably about 32 to 35°, at least one eighth intense peak with a 2θ value in a range of 40 to 45°, preferably 41 to 43°, or even more preferably about 42°, at least one ninth intense peak with a 2θ value in a range of 50 to 55°, preferably 51 to 54°, or even more preferably about 53°, at least one tenth intense peak with a 2θ value in a range of 55 to 60°, preferably 56 to 59°, or even more preferably about 57 to 58°, at least one eleventh intense peak with a 2θ value in a range of 60 to 65°, preferably 62 to 65°, or even more preferably about 63 to 65°, at least one twelfth intense peak with a 2θ value in a range of 65 to 80°, preferably 67 to 70°, or even more preferably about 68 to 69°, as depicted in FIGS. 2 and 3. Other ranges are also possible. In some embodiments, the intensity of the third peak of RM-2 is stronger than the intensity of the third peak of RM-1.

In some further embodiments, the red mud catalyst RM-3 has a first intense peak with a 2 theta (θ) value in a range of 5 to 10°, preferably about 8.5° in the XRD spectrum, a second intense peak with a 2θ value in a range of 12 to 15°, preferably about 13.5°, a third intense peak with a 2θ value in a range of 16 to 20°, preferably about 18.5°, a fourth intense peak with a 2θ value in a range of 20 to 23°, preferably about 22°, a fifth intense peak with a 2θ value in a range of 23 to 25°, preferably about 24.5°, a sixth intense peak with a 2θ value in a range of 25 to 27°, preferably about 26°, at least one seventh intense peak with a 2θ value in a range of 27 to 30°, preferably 28 to 29°, or even more preferably about 28.5°, at least one eighth intense peak with a 2θ value in a range of 32 to 35°, preferably 33 to 34°, or even more preferably about 33.5°, at least one ninth intense peak with a 2θ value in a range of 35 to 40°, preferably 35 to 38°, or even more preferably about 36.5°, at least one tenth intense peak with a 2θ value in a range of 40 to 50°, preferably 42 to 48°, or even more preferably about 44 to 46°, at least one eleventh intense peak with a 2θ value in a range of 50 to 60°, preferably 52 to 58°, or even more preferably about 54 to 56°, at least one twelfth intense peak with a 2θ value in a range of 60 to 80°, preferably 62 to 75°, or even more preferably about 64 to 70°, as depicted in FIG. 2. Other ranges are also possible. In some embodiments, the intensity of the third peak of RM-3 is stronger than the intensity of any other peaks in the XRD spectrum as depicted in FIG. 2.

FIG. 1A illustrates a schematic flow chart of a method 100 for chemically reducing $CO_2$ with a red mud catalyst composition. The order in which the method 100 described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes introducing a gaseous mixture of $CO_2$ and $H_2$ into a reactor containing particles of the red mud catalyst composition. Optionally, the gaseous mixture may also include other gases, such as CO, in addition to $CO_2$ and $H_2$. In some embodiments, the gaseous mixture, including $CO_2$ and $H_2$, is introduced into the reactor in a volumetric ratio of 1:10 to 10:1, preferably in a range of 1:1 to 1:6, preferably 1:5, preferably 1:4, and more preferably 1:3. Other ranges are also possible.

The reactor is at least one selected from the group consisting of a fixed-bed reactor, a trickle-bed reactor, a moving bed reactor, a rotating bed reactor, a fluidized bed reactor, and a slurry reactor. In an embodiment, the reactor may be an inclined tumbler reactor. In the present disclosure, the reactor is a fixed-bed reactor in the form of a cylindrical reactor which includes a top portion, a cylindrical body portion, a bottom portion, a housing. As used herein, the term 'fixed-bed reactor' refers to the cylindrical tube filled with catalyst pellets with reactants flowing through the bed and being converted into products. In some embodiments, the housing has an open top, and open bottom supportably maintained with the cylindrical body portion. The red mud catalyst composition is supportably retained within the housing, permitting fluid flow therethrough. In some embodiments, the cylindrical reactor further includes at least one propeller agitator disposed in the bottom portion of the reactor. In some embodiments, the main function of the propeller agitator is homogenization, dispersion, and suspension of low-viscosity products. In some embodiments, the bottom portion is cone-shaped or pyramidal. In an embodiment, the bottom portion may have a cylindrical, cubical, cuboidal, or rhombic shape. In some preferred embodiments, a plurality of recirculation tubes fluidly connects the bottom portion of the cylindrical reactor with the cylindrical body portion of the cylindrical reactor. In an embodiment, the cylindrical reactor may be a vertical cylindrical reactor, or a horizontal cylindrical reactor. In an embodiment, the fixed-bed reactor may be made up of a material such as stainless-steel, iron, aluminum, copper, lead, iron, zirconium, or another alloy.

Optionally, the red mud catalyst may be mixed with at least one material to form a catalyst composite for chemically reducing carbon dioxide ($CO_2$). In some embodiments, the at least one material is selected from the group consisting of carbon nanotubes, activated carbon, metal organic frameworks (MOFs), zeolitic imidazolate frameworks (ZIFs), different inorganic oxides, clays, covalent organic polymers (COPs) and their combinations. Examples of catalyst composite include carbon nanotube-complexed red mud catalyst, activated carbon-complexed red mud catalyst, MOF-complexed red mud catalyst, ZIF-complexed red mud catalyst, and COP-complexed red mud catalyst.

In general, the carbon nanomaterial may be any suitable carbon nanomaterial known to one of ordinary skill in the art. Examples of carbon nanomaterials include carbon nanotubes, carbon nanobuds, carbon nanoscrolls, carbon dots, activated carbon, carbon black, graphene, graphene oxide, reduced graphene oxide, and nanodiamonds. In some embodiments, the carbon nanomaterial is at least one selected from the group consisting of graphene, graphene oxide, reduced graphene oxide, carbon nanotubes, carbon dots, and activated carbon.

In some embodiments, the carbon nanomaterial is carbon nanotubes. The carbon nanotubes may, in general, be any suitable carbon nanotubes known to one of ordinary skill in the art. Carbon nanotubes may be classified by structural properties such as the number of walls or the geometric configuration of the atoms that make up the nanotube. Classified by their number of walls, the carbon nanotubes can be single-walled carbon nanotubes (SWCNT) which have only one layer of carbon atoms arranged into a tube, or multi-walled carbon nanotubes (MWCNT), which have more than one single-layer tube of carbon atoms arranged so as to be nested, one tube inside another, each tube sharing a common orientation. Closely related to MWNTs are carbon nanoscrolls. Carbon nanoscrolls are structures similar in shape to a MWCNT, but made of a single layer of carbon atoms that has been rolled onto itself to form a multi-layered tube with a free outer edge on the exterior of the nanoscroll and a free inner edge on the interior of the scroll and open ends. The end-on view of a carbon nanoscroll has a spiral-like shape. For the purposes of this disclosure, carbon nanoscrolls are considered a type of MWCNT. Classified by the geometric configuration of the atoms that make up the nanotube, carbon nanotubes can be described by a pair of integer indices n and m. The indices n and m denote the number of unit vectors along two directions in the honeycomb crystal lattice of a single layer of carbon atoms. If m=0, the nanotubes are called zigzag type nanotubes. If n=m, the nanotubes are called armchair type nanotubes. Otherwise, they are called chiral type nanotubes. In some embodiments, the carbon nanotubes are metallic. In other embodiments, the carbon nanotubes are semiconducting. In some embodiments, the carbon nanotubes are SWCNTs. In other embodiments, the carbon nanotubes are MWCNTs. In some embodiments, the carbon nanotubes are carbon nanoscrolls. In some embodiments, the carbon nanotubes are zigzag type nanotubes. In alternative embodiments, the carbon nanotubes are armchair type nanotubes. In other embodiments, the carbon nanotubes are chiral type nanotubes.

In some embodiments, the carbon nanomaterial is graphene. In some embodiments, the carbon nanomaterial is graphene nanosheets. Graphene nanosheets may consist of stacks of graphene sheets, the stacks having an average thickness and a diameter. In some embodiments, the stacks comprise 1 to 60 sheets of graphene, preferably 2 to 55 sheets of graphene, preferably 3 to 50 sheets of graphene.

In some embodiments, the graphene is in the form of graphene particles. The graphene particles may have a spherical shape, or may be shaped like blocks, flakes, ribbons, discs, granules, platelets, angular chunks, rectangular prisms, or some other shape. In some embodiments, the graphene particles may be substantially spherical, meaning that the distance from the graphene particle centroid (center of mass) to anywhere on the graphene outer surface varies by less than 30%, preferably by less than 20%, more preferably by less than 10% of the average distance. In some embodiments, the graphene particles may be in the form of agglomerates.

In some embodiments, the graphene is pristine graphene. Pristine graphene refers to graphene that has not been oxidized or otherwise functionalized. Pristine graphene may be obtained by methods such as exfoliation, chemical vapor deposition synthesis, opening of carbon nanotubes, unrolling of carbon nanoscrolls, and the like. In alternative embodiments, the graphene is functionalized graphene. Functionalized graphene is distinguished from pristine graphene by the presence of functional groups on the surface or edge of the graphene that contain elements other than carbon and hydrogen. In other alternative embodiments, the graphene is graphene oxide. Graphene oxide refers to graphene that has various oxygen-containing functionalities that are not present in pristine graphene. Examples of such oxygen-containing functionalities include epoxides, carbonyl, carboxyl, and hydroxyl functional groups. Graphene oxide is sometimes considered to be a type of functionalized graphene.

In other alternative embodiments, the graphene is reduced graphene oxide. Reduced graphene oxide (rGO) refers to graphene oxide that has been chemically reduced. It is distinct from graphene oxide in it contains substantially fewer oxygen-containing functionalities compared to graphene oxide, and it is distinct from pristine graphene by the presence of oxygen-containing functionalities and structural defects in the carbon network. Reduced graphene oxide is sometimes considered to be a type of functionalized graphene. In preferred embodiments, the carbon nanomaterial is reduced graphene oxide. The reduced graphene oxide may exist as nanosheets, particles having a spherical shape, or may be shaped like blocks, flakes, ribbons, discs, granules, platelets, angular chunks, rectangular prisms, or some other shape as described above, agglomerates as described above, or any other shape known to one of ordinary skill in the art.

In some embodiments, the carbon nanomaterial is activated carbon. Activated carbon refers to a form of porous carbon having a semi-crystalline, semi-graphitic structure and a large surface area. Activated carbon may be in the form of particles or particulate aggregates having micropores and/or mesopores. Activated carbon typically has a surface area of approximately 500 to 5000 $m^2/g$. The activated carbon particles may have a spherical shape, or may be shaped like sheets, blocks, flakes, ribbons, discs, granules, platelets, angular chunks, rectangular prisms, or some other shape. In some embodiments, the activated carbon particles may be substantially spherical, meaning that the distance from the activated carbon particle centroid (center of mass) to anywhere on the activated carbon particle outer surface varies by less than 30%, preferably by less than 20%, more preferably by less than 10% of the average distance.

In some embodiments, the carbon nanomaterial is carbon black. Carbon black refers to having a semi-crystalline, semi-graphitic structure and a large surface area. Carbon black may be distinguished from activated carbon by a comparatively lower surface area, typically 15 to 500 $m^2/g$ for carbon black. Additionally, carbon black may lack the requisite micropores and mesopores of activated carbon. The carbon black particles may have a spherical shape, or may be shaped like sheets, blocks, flakes, ribbons, discs, granules, platelets, angular chunks, rectangular prisms, or some other shape.

In some embodiments, the particles of a carbon nanomaterial are a single type of particle as described above. In this context, "a single type of particle" may refer to particles of a single carbon nanomaterial, particles which have substantially the same shape, particles which have substantially the same size, or any combination of these. In alternative embodiments, mixtures of types of particles are used.

As used herein, the term "zeolitic," "zeolite," "zeolitic materials," and similar terms generally refer to a material having the crystalline structure or three-dimensional framework of, but not necessarily the elemental composition of, a zeolite. Zeolites are porous silicate or aluminosilicate minerals that occur in nature. Elementary building units of zeolites are $SiO_4$ (and if appropriate, $AlO_4$) tetrahedra. Adjacent tetrahedra are linked at their corners via a common oxygen atom, which results in an inorganic macromolecule with a three-dimensional framework (frequently referred to as the zeolite framework). The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages. Zeolites which are devoid of aluminum may be referred to as "all-silica zeolites" or "aluminum-free zeolites". Some zeolites which are substantially free of, but not devoid of, aluminum are referred to as "high-silica zeolites". Sometimes, the term "zeolite" is used to refer exclusively to aluminosilicate materials, excluding aluminum-free zeolites or all-silica zeolites.

In some embodiments, the zeolitic material has a three-dimensional framework that is at least one zeolite framework selected from the group consisting of a 4-membered ring zeolite framework, a 6-membered ring zeolite framework, a 10-membered ring zeolite framework, and a 12-membered ring zeolite framework. The zeolite may have a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g. analcime, leucite, pollucite, and wairakite), phillipsite framework (e.g. harmotome), gismondine framework (e.g. amicite, gismondine, garronite, and gobbinsite), chabazite framework (e.g. chabazite-series, herschelite, willhendersonite, and SSZ-13), faujasite framework (e.g. faujasite-series, Linde type X, and Linde type Y), mordenite framework (e.g. maricopaite and mordenite), heulandite framework (e.g. clinoptilolite and heulandite-series), stilbite framework (e.g. barrerite, stellerite, and stilbite-series), brewsterite framework, or cowlesite framework. In some embodiments, the porous silicate and/or aluminosilicate matrix is a zeolitic material having a zeolite framework selected from the group consisting of ZSM-5, ZSM-8, ZSM-11, ZSM-12, ZSM-18, ZSM-23, ZSM-35 and ZSM-39.

The International Union of Pure and Applied Chemistry (IUPAC) states that a metal organic framework (MOF) is a coordination network with organic ligands containing potential voids. A coordination network is a coordination compound extending, through repeating coordination entities, in one dimension, but with cross-links between two or more individual chains, loops, or spiro-links, or a coordination compound extending through repeating coordination entities in two or three dimensions; and finally a coordination polymer is a coordination compound with repeating coordination entities extending in one, two, or three dimensions. A coordination entity is an ion or neutral molecule that is composed of a central atom, usually that of a metal, to which is attached a surrounding array of atoms or groups of atoms, each of which is called ligands. More succinctly, a metal organic framework is characterized by metal ions or clusters coordinated to organic ligands to form one-, two-, or three-dimensional structures. Typically, a MOF exhibits a regular void or pore structure. The nature of the void or pore structure, including properties or structural factors such as the geometry about the metal ions or clusters, the arrangement of the linkages between metal ions or clusters, and the number, identity, and spatial arrangement of voids or pores. These properties may be described as the structure of the repeat units and the nature of the arrangement of the repeat units. The specific structure of the MOF, which may include the void or pore structure is typically referred to as the MOF topology.

The metal-organic framework comprises a metal ion which is an ion of at least one metal selected from the group consisting of a transition metal (e.g. Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, db, Sg, Bh, Hs, Mt, Ds, Rg, and Cn), a post-transition metal (e.g. Al, In, Ga, Sn, Bi, Pb, Tl, Zn, Cd, and Hg), and an alkaline earth metal (e.g. Be, Mg, Ca, Sr, Ba, and Ra). Further, these metal ions may be of any oxidation state $M^{+1}$, $M^{+2}$, $M^{+3}$, etc. In one or more embodiments, the metal ion is an ion of at least one metal selected from the group consisting of Zn, Cu, Fe, Ni, Co, Mn, Cr, Cd, Mg, Ca, and Zr.

In the formation of a metal organic framework, the organic ligands must meet certain requirements to form coordination bonds, primarily being multi-dentate, having at least two donor atoms (i.e. N—, and/or O—) and being neutral or anionic. The structure of the metal organic framework is also affected by the shape, length, and functional groups present in the organic linker. In certain embodiments, the metal organic framework of the present disclosure comprises anionic ligands as organic ligands. In one or more embodiments, the organic ligands may have at least two nitrogen donor atoms. For example, the organic ligands may be imidazolate-based, imidazole-derived or ligands similar to an imidazole including, but not limited to, optionally substituted imidazoles, optionally substituted benzimidazoles, optionally substituted imidazolines, optionally substituted pyrazoles, optionally substituted thiazoles, and optionally substituted triazoles. In a preferred embodiment, the metal organic framework of the present disclosure in any of its embodiments comprises 2-methylimidazole and 5-methylbenzimidazole as the organic ligands. 2-Methylimidazole and 5-methylbenzimidazole organic ligands have free nitrogen atoms that may each form a coordinative bond to the metal ions (e.g. Zn(II)) to produce a coordination network.

Metal organic frameworks comprising such imidazole or benzimidazole ligands are typically referred to as zeolitic imidazolate frameworks (ZIFs). In some embodiments, the metal organic framework is a zeolitic imidazolate framework. Examples of suitable metal organic frameworks include, but are not limited to isoreticular metal organic framework-3 (IRMOF-3), MOF-69A, MOF-69B, MOF-69C, MOF-70, MOF-71, MOF-73, MOF-74, MOF-75, MOF-76, MOF-77, MOF-78, MOF-79, MOF-80, DMOF-1-NH$_2$, UMCM-1-NH$_2$, MOF-69-80, ZIF-1, ZIF-2, ZIF-3, ZIF-4, ZIF-5, ZIF-6, ZIF-7, ZIF-9, ZIF-10, ZIF-11, ZIF-12, ZIF-14, ZIF-20, ZIF-21, ZIF-22, ZIF-23, ZIF-25, ZIF-60, ZIF-61, ZIF-62, ZIF-63, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-77, ZIF-78, ZIF-79, ZIF-80, ZIF-81, ZIF-82, ZIF-90, ZIF-91, ZIF-92, ZIF-93, ZIF-94, ZIF-96, ZIF-97, ZIF-100, ZIF-108, ZIF-303, ZIF-360, ZIF-365, ZIF-376, ZIF-386, ZIF-408, ZIF-410, ZIF-412, ZIF-413, ZIF-414, ZIF-486, ZIF-516, ZIF-586, ZIF-615, and ZIF-725.

In some embodiments, the material is aluminum oxide. In some embodiments, the aluminum oxide is gamma (γ) aluminum oxide. These can include substances serving as a granulating agent or a binder. Examples thereof include alumina, silica, titania, silica-alumina, alumina-titania, alumina-zirconia, alumina-boria, phosphorus-alumina, silica alumina-boria, phosphorus-alumina-boria, phosphorus-alumina-silica, silica-alumina-titania, and silica-alumina-zirconia.

In some embodiment, the red mud material is modified by directly impregnating with one metal or their combinations selected from the group consisting of a transition metal (e.g. Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, db, Sg, Bh, Hs, Mt, Ds, Rg, and Cn), a post-transition metal (e.g. Al, In, Ga, Sn, Bi, Pb, Tl, Zn, Cd, and Hg), and an alkaline earth metal (e.g. Be, Mg, Ca, Sr, Ba, and Ra). Further, these metal ions may be of any oxidation state $M^{+1}$, $M^{+2}$, $M^{+3}$, etc. In one or more embodiments, the metal ion is an ion of at least one metal selected from the group consisting of Zn, Cu, Fe, Ni, Co, Mn, Cr, Cd, Mg, Ca, and Zr.

In some embodiments, the material is present in the form of particles. In general, the particles can be any shape known to one of ordinary skill in the art. Examples of suitable shapes the metal organic framework particles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, nanotubes, blocks, flakes, discs, granules, angular chunks, and mixtures thereof.

In some embodiments, the material particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of material particles having a different shape. As used herein, the term "non-uniform shape" refers to an average consistent shape that differs by more than 10% of the distribution of material particles having a different shape. In one embodiment, the shape is uniform and at least 90% of the material particles are spherical or substantially circular, and less than 10% are polygonal. In another embodiment, the shape is non-uniform and less than 90% of the material particles are spherical or substantially circular, and greater than 10% are polygonal.

At step 104, the method 100 includes reacting at least a portion of the $CO_2$ and $H_2$ in the gaseous mixture in the presence of the red mud catalyst composition to form a gaseous product including a chemical reduction product of the $CO_2$. During operation, the reactor was maintained at a temperature range of 200-800° C., preferably 250-750° C., preferably 280-500° C., preferably 300 to 450° C., and more preferably 300 to 450° C. during operation. Other ranges are also possible. Likewise, the pressure in the reactor was between 5 to 100 bars, preferably 10-50 bars, preferably 15-45 bars, preferably 20-44 bars, preferably 25-40 bars, and more preferably between 30-40 bars during operation. Other ranges are also possible.

In some embodiments, the reaction yields a gaseous product that includes methane, ethane, ethylene, propane, propylene, carbon monoxide, a hydrocarbon containing $C_4$-$C_9$ such as butane, butene, pentane, and pentene; and aromatics such as benzene, naphthalene, anthracene, or their isomers, or mixtures of these substance. In some embodiments, the C4-C9 hydrocarbon contains butane, butene, butyne, pentane, pentene, pentyne, hexane, hexene, hexyne, cyclohexane, cyclohexene, heptane, heptene, heptyne, octane, octene, octyne, nonane, nonene, nonyne, or their isomers, or mixtures of these substance.

In some embodiments, the methane is present in the gaseous product at a concentration of 20 to 50 wt. %, more preferably 24 to 45 wt. %, preferably 25 to 43 wt. %, preferably 27 to 32 wt. %, and carbon monoxide is present in the gaseous product at a concentration of 25 to 50 wt. %, more preferably 30 to 49 wt. %, and yet more preferably 32 to 47 wt. %, each wt. % based on total weight of the gaseous product. Other ranges are also possible. The method 100 of the present disclosure chemically reduces 10 to 25%, more preferably 10 to 20%, and yet more preferably 12 to 15 wt. %, of the $CO_2$ based on a total weight of the gaseous mixture. Other ranges are also possible.

In some embodiments, the gaseous product contains about 40 to 44 wt. % of methane, 10 to 14 wt. % of ethane, 0.5 to 2 wt. % of ethylene, 3 to 7 wt. % of propane, 0.5 to 4 wt. % of propylene, 2 to 6 wt. % of C4+C5, less than 0.15 wt. % of aromatics, and 30 to 35 wt. % of CO, each wt. % based on total weight of the gaseous product. Other ranges are also possible.

In some further embodiments, the gaseous product contains about 25 to 33 wt. % of methane, 3 to 9 wt. % of ethane, 7 to 11 wt. % of ethylene, 1 to 3 wt. % of propane, 7 to 11 wt. % of propylene, 2 to 6 wt. % of C4+C5, 0.15 to 1 wt. % of aromatics, and 40 to 45 wt. % of CO, each wt. % based on total weight of the gaseous product. Other ranges are also possible.

In some preferred embodiments, the gaseous product contains about 25 to 31 wt. % of methane, 4 to 8 wt. % of ethane, 5 to 9 wt. % of ethylene, 1 to 3 wt. % of propane, 5 to 10 wt. % of propylene, 2 to 6 wt. % of C4+C5, 0.3 to 0.8 wt. % of aromatics, and 42 to 50 wt. % of CO, each wt. % based on total weight of the gaseous product. Other ranges are also possible.

In some more preferred embodiments, the gaseous product contains about 28 to 36 wt. % of methane, 2 to 4 wt. % of ethane, 9 to 15 wt. % of ethylene, 1 to 3 wt. % of propane, 9 to 13 wt. % of propylene, 0.02 to 0.2 wt. % of C4+C5, 0.5 to 1.1 wt. % of aromatics, and 30 to 35 wt. % of CO, each wt. % based on total weight of the gaseous product. Other ranges are also possible.

Figure 1B:
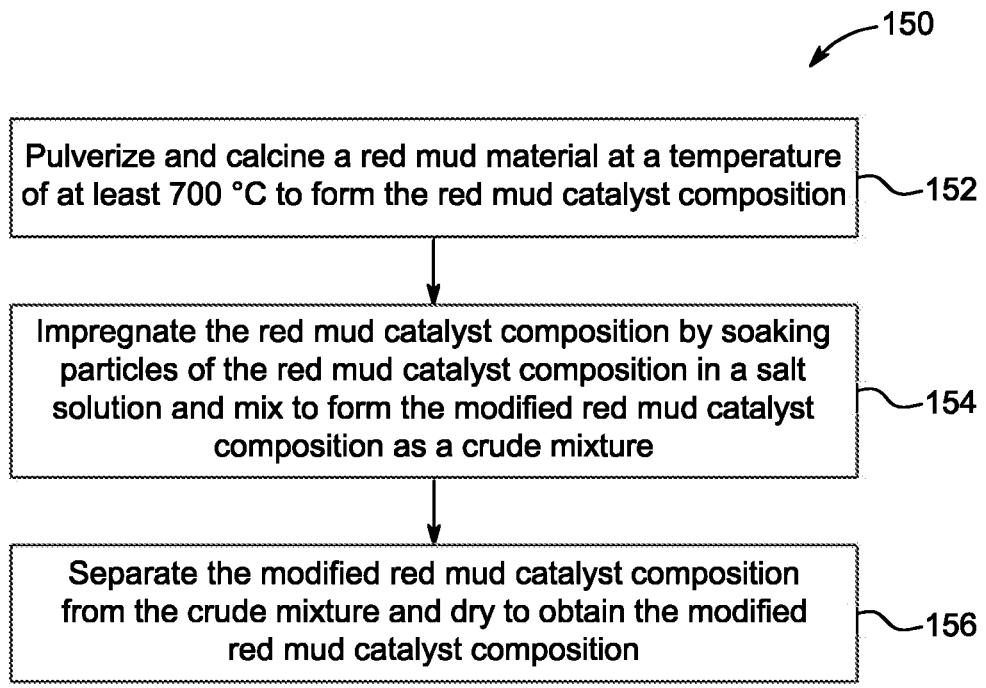
FIG. 1B is a flowchart depicting a method for preparing the red mud catalyst composition, according to certain embodiments.

FIG. 1B illustrates a schematic flow chart of a method 150 for preparing a modified red mud catalyst composition. The order in which the method 150 described is not intended to be construed as a limitation, and any number of the described method steps can be combined in any order to implement the method 150. Additionally, individual steps may be removed or skipped from the method 150 without departing from the spirit and scope of the present disclosure.

At step 152, the method 150 includes pulverizing and calcining a red mud material at a temperature of at least 700° C. to form the red mud catalyst composition. As used herein, the term 'pulverization' refers to applying an external force to a solid material of a certain size to break up the solid material and reduce the solid material into pieces smaller than the original size. The pulverization may be carried out using any suitable means, for example, by grinding, ball milling, blending, etc., using manual methods (e.g., mortar) or machine-assisted methods such as using a mechanical blender, or any other apparatus known to those of ordinary skill in the art. In some embodiments, the pulverization is carried out till the particle size of the red mud particles is reduced to a micrometer level. Further to pulverization, the red mud material is calcined by subjecting the micrometer-sized red mud material by heating it to a high temperature, under a restricted supply of ambient oxygen. This was performed to remove impurities or volatile substances and to incur thermal decomposition. In some embodiments, the calcination is carried out in a furnace preferably equipped with a temperature control system, which may provide a heating rate of up to 50° C./min, or preferably up to 40° C./min, or preferably up to 30° C./min, preferably up to 20° C./min, preferably up to 10° C./min, preferably up to 5° C./min. Other ranges are also possible. In preferred embodiments, the mixed powders are heated with a heating rate in the range of 1 to 15° C./min, preferably 3 to 10° C./min, preferably 5 to 6° C./min to a temperature range of 500 to 1,000° C., preferably 600 to 975° C., preferably 650 to 950° C., preferably 675 to 925° C., preferably 700° C. for 1 to 15 hours, preferably 2 to 10 hours, preferably 3 to 8 hours, preferably 4 to 6 hours, preferably 6 hours. Other ranges are also possible.

At step 154, the method 150 includes impregnating the red mud catalyst composition by soaking particles of the red mud catalyst composition in a salt solution and mixing to form the modified red mud catalyst composition as a crude mixture. To bring about impregnation of the alkali metals on the red mud catalyst composition, the red mud catalyst composition is soaked in the salt solution. In some embodiments, the salt solution includes at least one salt selected from the group consisting of an alkali metal salt and an alkaline earth metal salt. In some further embodiments, the alkali metal salt may include sodium carbonate, sodium acetate, sodium sulfide, sodium bicarbonate, sodium hydroxide, potassium cyanide, and/or combinations thereof. In some preferred embodiments, the alkaline earth metal salt may include, but are not limited to, epsom salt, gypsum, beryllium aluminum silicate, beryllium silicate hydroxide, carnalite, dolomite, magnesite, magnesium hydroxide, strontium sulfate, strontium carbonate, barium sulfate, barium carbonate and mixtures thereof. In some more preferred embodiments, the salt solution includes at least one salt selected from the group consisting of potassium fluoride (KF), potassium chloride (KCl), potassium bromide (KBr), potassium nitrate ($KNO_3$), potassium sulfate ($K_2SO_4$), potassium carbonate ($K_2CO_3$), potassium phosphate ($K_3PO_4$), and potassium hydroxide (KOH). In some further preferred embodiments, the salt is present in the salt solution at a concentration of 0.5 to 10 wt. %, more preferably 5 to 9%, and yet more preferably 6 to 8%, based on the total weight of the salt solution. Other ranges are also possible. In some further preferred embodiments, the red mud catalyst composition is soaked in the salt solution till such a time, about 10-60 minutes, preferably 20-40 minutes, and more preferably for about 30 minutes, till the alkali metal is adsorbed on the surface of the red mud catalyst composition. Other ranges are also possible. In some further preferred embodiments, other conventionally known methods of impregnation may be adopted as well, as may be obvious to a person skilled in the art.

At step 156, the method 150 includes separating the modified red mud catalyst composition from the crude mixture and then drying the crude mixture to obtain the modified red mud catalyst composition. In some embodiments, the modified red mud catalyst composition may be separated from the crude mixture via centrifugation, filtration, evaporation, or by a method used or known in the art. In some further embodiments, the separated modified red mud catalyst composition is further dried to a temperature range of 60-120° C., preferably 70-110° C., preferably 80-100° C., and more preferably to about 90° C. for a period of 12 to 16 hours to remove any water molecules/volatile components in the modified red mud catalyst composition. Other ranges are also possible. In addition, the modified red mud catalyst may be dried in a heating device such as ovens, hot plates, heating mantles and tapes, oil baths, salt baths, sand baths, air baths, hot-tube furnaces, hot-air guns, and microwave ovens.

The catalytic activity of two sets of catalysts was evaluated in $CO_2$ reduction. The first set of catalyst is the red mud catalyst composition that are used without any modification, while the second set of catalysts are modified red mud catalysts including impregnated red mud catalysts with a salt, e.g., potassium, to form potassium promoted catalyst. The catalysts are characterized using inductively coupled plasma optical emission spectroscopy (ICP-OES), X-ray diffraction (XRD), temperature program reduction using $H_2$ ($H_2$-TPR), and $N_2$ adsorption/desorption method for calculating the structure, reducibility/$H_2$ uptake of the first set catalysts and Brunauer-Emmett-Teller (BET) surface area, respectively, while the second set of catalysts is characterized using $CO_2$-TPD and $NH_3$-TPD. Basicity and acidity of the first set catalysts are analyzed using temperature program desorption using carbon dioxide ($CO_2$-TPD) and ammonia ($NH_3$-TPD), respectively, to determine the physicochemical properties. Both sets of catalysts are tested for their performance in $CO_2$ hydrogenation application using a fixed-bed reactor at the desired temperature and pressure in down-flow mode using a feed containing $CO_2$ and $H_2$.

As used herein, the term "inductively coupled plasma optical emission spectroscopy," or "ICP-OES" generally refers to a technique used to determine the elemental composition of a sample, such as a red mud catalyst. In some embodiments, the red mud catalyst is atomized and excited in an inductively coupled plasma (ICP), which is a high-temperature argon gas plasma generated by an electrical discharge. In some further embodiments, the excited atoms emit light at characteristic wavelengths that are specific to each element. In some preferred embodiments, the emitted light is then separated into its component wavelengths using a spectrometer, and the intensity of the emitted light is measured to determine the concentration of each element in the red mud catalyst.

As used herein, the term "$N_2$ adsorption/desorption method" generally refers to a technique used to measure the specific surface area of a solid material, such as a catalyst or a porous material. In some embodiments, the red mud catalyst is exposed to a stream of nitrogen gas at low temperature and pressure. The nitrogen gas is adsorbed onto the surface of the red mud catalyst, filling the pores and creating a monolayer of adsorbed nitrogen. In some further embodiments, the amount of nitrogen adsorbed at a given pressure is measured using a gas adsorption instrument, such as a BET instrument. In some preferred embodiments, the BET analysis is performed on a BELSORP analyzer according to the software manual, pages 62 to 66, manufactured by Bell Japan. In some more preferred embodiments, the nitrogen gas is gradually removed from the red mud catalyst, causing the desorption of the adsorbed nitrogen. The amount of nitrogen desorbed at a given pressure is also measured using the gas adsorption instrument. By analyzing the amount of nitrogen adsorbed and desorbed, the specific surface area of the red mud catalyst can be calculated using the BET (Brunauer-Emmett-Teller) and Barrett, Joyner and Halenda (BJH) equation.

The red mud catalyst composition was characterized by various analytical techniques, one among which is hydrogen temperature-programmed reduction ($H_2$-TPR). As used herein, the term "temperature program reduction using $H_2$," or "$H_2$-TPR" generally refers to a technique used to study the reducibility of a solid material, such as a red mud catalyst, by measuring the consumption of a reducing gas, such as hydrogen, as a function of temperature. In some embodiments, the red mud catalyst is first heated in an oxidizing gas, such as air or oxygen, to remove any adsorbed species and to convert the red mud catalyst to an oxide. In some further embodiments, the oxidized red mud catalyst is then cooled down and exposed to a stream of hydrogen gas, while the temperature is gradually increased. As the temperature increases, the hydrogen reacts with the oxidized red mud catalyst, causing a reduction of the material. In some preferred embodiments, this reduction reaction may be exothermic, and the heat generated by the reaction is monitored as a function of temperature.

Figure 5:
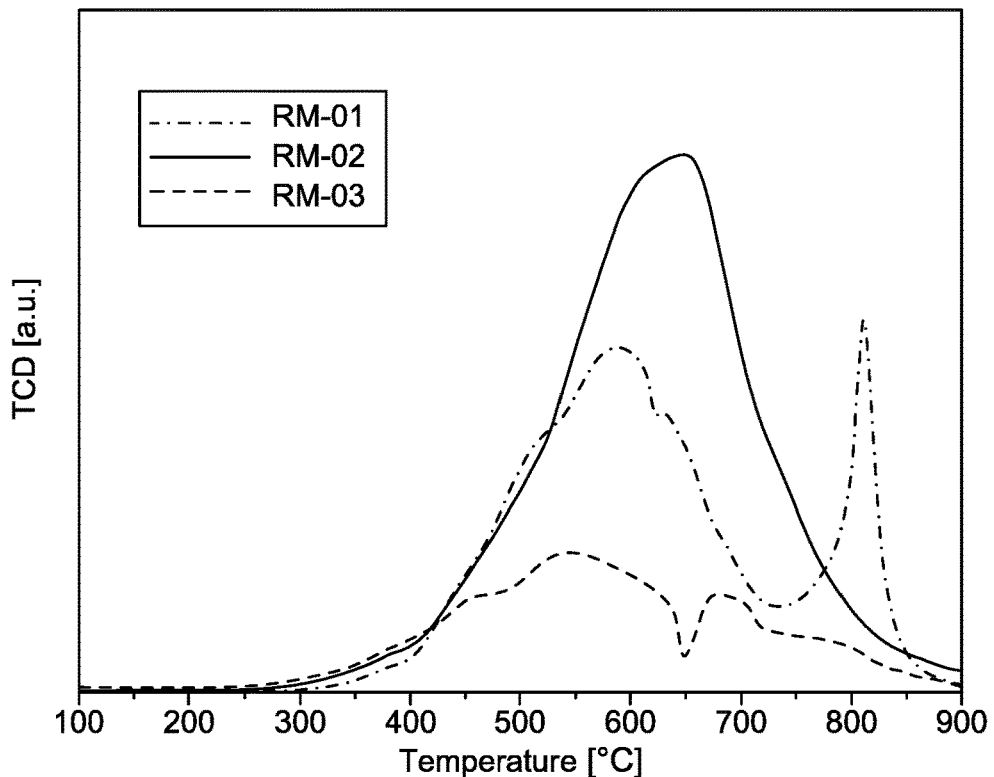
FIG. 5 depicts hydrogen-temperature programmed reduction ($H_2$-TPR) plots of the red mud samples, according to certain embodiments.

Referring to FIG. 5, hydrogen-temperature programmed reduction ($H_2$-TPR) plots of the red mud samples. In some embodiments, the $H_2$-TPR was conducted on a BellCat chemisorption analyzer. The red mud catalyst was placed in a quartz calcined at a temperature of 400 to 800° C., preferably 450 to 750° C., preferably 500 to 700° C., preferably 550 to 650° C., or even more preferably about 600° C. under an argon flow for at least 30 minutes, at least 60 minutes, at least 120 minutes. In some further embodiments, the red mud catalyst was cooled to a temperature of no more than 70° C., preferably no more than 60° C., or even more preferably no more than 50° C. In some preferred embodiments, a gas flow contains hydrogen ($H_2$) and argon (Ar) in a volumetric ratio of $H_2$ to Ar ranging from 1:20 to 1:1, preferably 1:15 to 1:5, or even more preferably about 1:10 was introduced to flow over the red mud catalyst at a flow rate of 10 to 60 cubic centimeters per minutes (cm³/min), preferably 20 to 50 cm³/min, or even more preferably about 30 cm³/min. In some preferred embodiments, the temperature of the analyzer containing the red mud catalyst was increased at ramping rate of 5 to 20° C. per minute until the temperature reaches about 900° C. Other ranges are also possible. In some most preferred embodiments, the composition of the present disclosure has an $H_2$-TPR in a range of 0.5 to 5 mmol/g, preferably 0.7 to 4.5 mmol/g, preferably 1 to 4 mmol/g, and more preferably 1.34 to 3.89 mmol/g, as depicted in FIG. 5. Other ranges are also possible.

As used herein, the term "temperature program desorption using carbon dioxide," or "$CO_2$-TPD" generally refers to a technique used to study the surface acidity of a solid material, such as a red mud catalyst. In some embodiments, the red mud catalyst is first heated in an inert gas, such as nitrogen, to remove any adsorbed species and to stabilize the surface. In some embodiments, the red mud catalyst is then cooled down and exposed to a stream of carbon dioxide gas, which is adsorbed onto the surface of the red mud catalyst. The amount of carbon dioxide adsorbed is proportional to the surface acidity of the red mud catalyst. The red mud catalyst is then heated at a constant rate while the amount of carbon dioxide desorbed is monitored as a function of temperature. In some further embodiments, as the temperature increases, the adsorbed carbon dioxide begins to desorb from the surface of the red mud catalyst. In some preferred embodiments, the desorption of carbon dioxide may be exothermic, and the heat generated by the desorption process is monitored using a thermal conductivity detector.

As used herein, the term "temperature program desorption using ammonia," or "$NH_3$-TPD" generally refers to a technique used to study the surface basicity of a solid material, such as a red mud catalyst. In some embodiments, the red mud catalyst is first heated in an inert gas, such as nitrogen, to remove any adsorbed species and to stabilize the surface. In some embodiments, the red mud catalyst is then cooled down and exposed to a stream of ammonia gas, which is adsorbed onto the surface of the red mud catalyst. The amount of ammonia adsorbed is proportional to the surface basicity of the red mud catalyst. In some embodiments, the red mud catalyst is then heated at a constant rate while the amount of ammonia desorbed is monitored as a function of temperature. In some further embodiments, ss the temperature increases, the adsorbed ammonia begins to desorb from the surface of the red mud catalyst. In some preferred embodiments, the desorption of ammonia may be exothermic, and the heat generated by the desorption process is monitored using a thermal conductivity detector.

The modified red mud catalyst was characterized mainly using $CO_2$-TPD and $NH_3$-TPD. Temperature programmed desorption (TPD) is a technique used to monitor surface interactions between molecular species on a surface when the surface temperature has changed in a controlled setting. This technique determines the strength of interactions between the red mud catalyst composition and the alkali metal adsorbed on the red mud catalyst composition. This is done by placing the modified red mud catalyst composition inside a reactor and pushing an inert gas into the chamber. Alternatively, the sample can be located in an ultra-high vacuum (UHV) chamber with no carrier gas. The sample is dosed with a probe gas such as CO, $NH_3$, $H_2$, etc. The sample is then increased in temperature at a linear ramp rate, and the desorption products are analyzed by a mass spectrometer.

Figure 6:
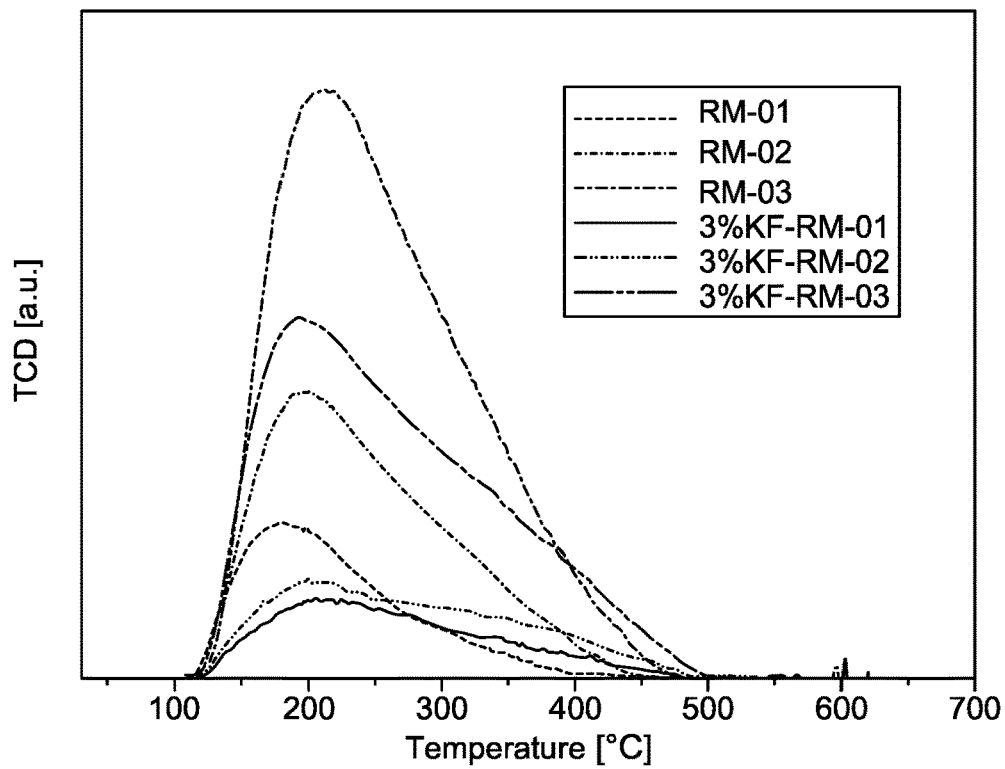
FIG. 6 depicts temperature-programmed desorption of ammonia ($NH_3$-TPD) plot of the red mud samples, according to certain embodiments.

FIG. 6 illustrates a temperature-programmed desorption of ammonia ($NH_3$-TPD) plot of the red mud samples. The $NH_3$-TPD was conducted on a MicrotracBEL equipment. The red mud catalyst was heated at a temperature of 500 to 600° C., preferably about 550° C. under a helium gas flow for 30 to 90 min, preferably about 60 min at a flow rate of 30 to 70 milliliters per minute (mL/min), preferably 50 mL/min. Other ranges are also possible. In some further embodiments, the red mud catalyst was then cooled to less than 150° C., preferably less than 100° C. before contacting with a $NH_3$-containing gas mixture. In some preferred embodiments, $NH_3$ is present in the gas mixture at a concentration of 1 to 20%, preferably about 5 to 15%, or even more preferably about 10% by volume. In some more preferred embodiments, the MicrotracBEL equipment containing the red mud samples is heated to a temperature of 600 to 700° C., preferably about 650° C. at a heating rate of 5 to 30° C./min, preferably 5 to 20° C./min, or even more preferably about 10° C./min. Other ranges are also possible. In some most preferred embodiments, the red mud catalyst composition has a temperature-programmed desorption of ammonia ($NH_3$-TPD) of 0.001 to 0.1 mmol/g, more preferably 0.001 to 0.01 mmol/g, and yet more preferably 0.004 to 0.01 mmol/g, as depicted in FIG. 6. Other ranges are also possible.

Figure 7:
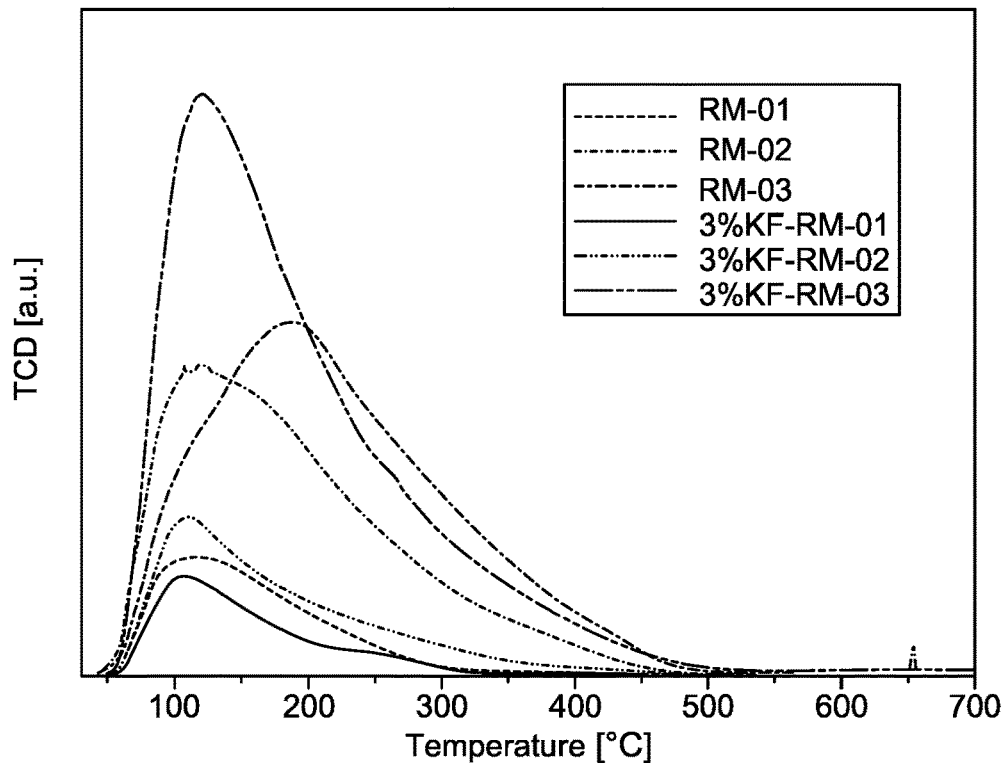
FIG. 7 depicts temperature-programmed desorption of carbon dioxide ($CO_2$-TPD) plot of the red mud samples, according to certain embodiments.

FIG. 7 illustrates a temperature-programmed desorption of carbon dioxide ($CO_2$-TPD) plot of the red mud samples. In some embodiments, the $CO_2$-TPD is performed by saturating the red mud catalyst in a $CO_2$ atmosphere at a temperature of 25 to 65° C., preferably about 45° C. In some further embodiments, the red mud catalyst after saturation was flushed with a carrier gas for 5 to 60 min, or even more preferably about 30 min to remove physically adsorbed $CO_2$. In some more preferred embodiments, the red mud catalyst after saturation was heated to a temperature of 600 to 800° C., or even more preferably about 700° C. to desorb $CO_2$. In some most preferred 5 embodiments, the red mud catalyst composition has a temperature-programmed desorption of carbon dioxide ($CO_2$-TPD) of 0.01 to 0.5 mmol/g, more preferably 0.03 to 0.3 mmol/g, and yet more preferably 0.1 to 0.25 mmol/g, as depicted in FIG. 7. Other ranges are also possible.

Examples

The following examples describe and demonstrate exemplary embodiments of the method 100 described herein. The examples are provided solely for the purpose of illustration and are not to be construed as limitations of the present disclosure, as many variations thereof are possible without departing from the spirit and scope of the present disclosure.

Example 1: Elemental Composition of Red Mud Samples

Three samples of red mud samples were collected from three different geographical locations and are named RM-1, RM-2, and RM-3. For elemental analysis, the raw materials are separately extracted to an aqueous solution using acid mixtures and quantitatively analyzed using ICP-OES. The important metals and their concentrations, in each of the samples, are presented in Table 1. Major metals present are Fe, Al, and Na, whereas metals like V, C, Mg, and P were also detected at various levels in each sample.

TABLE 1

Elemental composition of the red mud samples

| Sample Name | Elements present in the mud samples (% w/w) | | | | | | | | | |
|---|---|---|---|---|---|---|---|---|---|---|
| | Al | Fe | Mg | Mn | Na | P | Ti | V | C | S |
| RM-1 | 9.83 | 14.87 | 0.18 | ND | 7.66 | 0.19 | 3.86 | 0.16 | 0.98 | 0.16 |
| RM-2 | 7.98 | 23.88 | 0.13 | ND | 6.56 | 0.05 | 1.37 | 0.13 | 1.98 | 0.14 |
| RM-3 | 18.77 | 4.98 | 0.07 | ND | 4.47 | 0.05 | 0.49 | 0.05 | 2.57 | 0.12 |

Example 2: Preparation of the Catalyst

Each red mud sample was separately crushed and then calcined at 700° C. for 6 hours at a ramping rate of 5° C. per minute and used directly as catalytic materials named as RM-1, RM-2, and RM-3 (unmodified catalysts). To prepare the modified catalysts, 3 wt. % of KF was loaded over each of the red mud powders, separately by using the wet impregnation method; the required amount of the KF was dissolved in 10 ml of de-ionized water and then added to the red mud samples. All samples were left to soak for 30 minutes and then thoroughly mixed using a glass rod. A magnetic stirrer was not used to avoid the separation of irons. Finally, the samples were dried overnight at 90° C. Catalyst samples prepared using RM-1, RM-2, and RM-3 are named as Cat-1 or 3% KF-RM-01, Cat-2 or 3% KF-RM-02, and Cat-3 or 3% KF-RM-03, respectively.

Example 3: Characterization of the Catalyst Samples

Structural properties, reducibility/$H_2$ consumption, acidity/basicity, and surface area/porosity are investigated by the respective techniques before the catalytic evaluation of the prepared catalysts. An X-ray diffractometer (XRD, Miniflex from Rigaku) equipped with Cu Kα radiation (λ=0.15406 nm) was used to get the diffraction patterns of the red mud samples, which are given in FIG. 2 with zoomed profiles of RM-1 and RM-2 as provided in FIG. 3. FIG. 2 and FIG. 3 show that all the samples are crystalline in nature.

Figure 4:
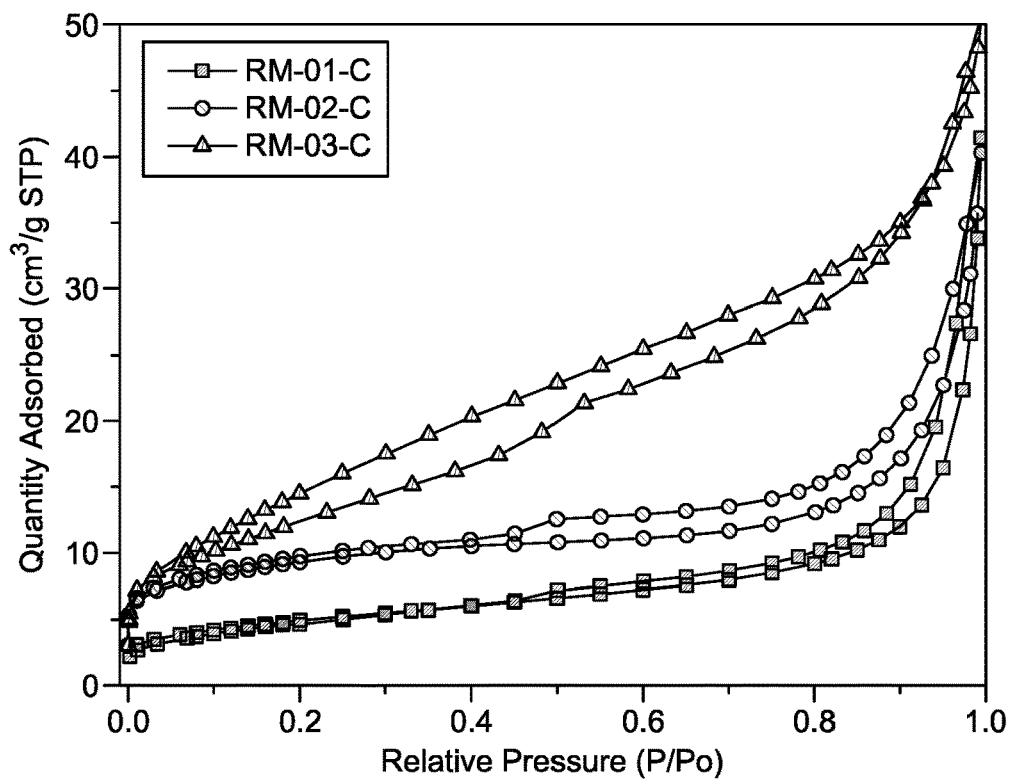
FIG. 4 depicts a nitrogen adsorption isotherm plot of the red mud samples, according to certain embodiments.

The surface areas and pore volumes of the samples were analyzed using the $N_2$ adsorption method and are calculated using the BET and Barrett, Joyner, and Halenda (BJH) equation. The samples were degassed at 300° C. for 12 hours, and the analysis was performed in a liquid $N_2$ bath at −195.8° C. BET/BJH results are given in FIG. 4 and Table 2.

TABLE 2

Surface area, pore volume, and $H_2$-TPR results

| Sample | BET Surface Area (m$^2$/g) | Pore volume (cm$^3$/g) | $H_2$-TPR (mmol/g) |
|---|---|---|---|
| RM-1 | 16.6 | 0.035 | 2.88 |
| RM-2 | 32.6 | 0.044 | 3.89 |
| RM-3 | 58.0 | 0.067 | 1.34 |

$H_2$-TPR was conducted using a BelCat chemisorption analyzer. Around 50 milligrams (mg) of the samples were placed in quartz calcined at 600° C. under the flow of Ar for 1 hour. Then, the samples were cooled down to 50° C. Following this, a gas consisting of 10 vol. % $H_2$ and 90 vol. % Ar was allowed to flow over the samples at a flow rate of 30 cm$^3$/min, and the temperature was ramped at a ramping rate of 10° per minute up to 900° C. The $H_2$ consumed with the temperature increase was measured using a thermal conductivity detector (TCD) detector, and the results are provided in FIG. 5 and Table 2. $H_2$-TPR results show the presence of reducible metals and their ability to adsorb and consume $H_2$ during a catalytic reaction.

The acidity of the samples is determined using Microtrac-BEL equipment, by using about 50 mg of the sample, pre-treated at 550° C. in the presence of continuous flow of helium gas for 60 min at a flow rate of 50 milliliters per minute (mL/min). After that, the sample was cooled to 100° C. followed by the adsorption of the $NH_3$ mixture for 30 min (10% $NH_3$ in helium, 50 mL/min). The physiosorbed gases were flushed with helium gas for 45 min with a helium flow rate of 30 ml/min. Finally, the sample was heated to 650° C. at a constant heating rate of 10° C. min$^{-1}$ to desorb the $NH_3$ from the sample, and simultaneously, the TPD signal was monitored by a TCD. The results of this study are shown in Table 3 and FIG. 6.

TABLE 3

Ammonia and $CO_2$ TPD results

| Sample | $NH_3$-TPD (mmol/g) | $CO_2$-TPD (mmol/g) |
|---|---|---|
| RM-1 | 0.004 | 0.051 |
| RM-2 | 0.010 | 0.177 |
| RM-3 | 0.021 | 0.233 |
| 3% KF-RM-01 | 0.003 | 0.036 |
| 3% KF-RM-02 | 0.004 | 0.070 |
| 3% KF-RM-03 | 0.014 | 0.293 |

The affinity of the samples for $CO_2$ uptake was studied by adsorption and desorption of $CO_2$ ($CO_2$-TPD) with the increase in temperature. The samples were saturated with $CO_2$ at 45° C. Thereafter, the samples were flashed with carrier gas for 30 min to remove the physically adsorbed $CO_2$. Finally, the saturated samples were heated up to 700° C., and the desorbed $CO_2$ was measured using a TCD. The overlaid desorption plots are given in FIG. 7 and Table 3.

Example 4: Performance Testing of the Red Mud Samples

Figure 8:
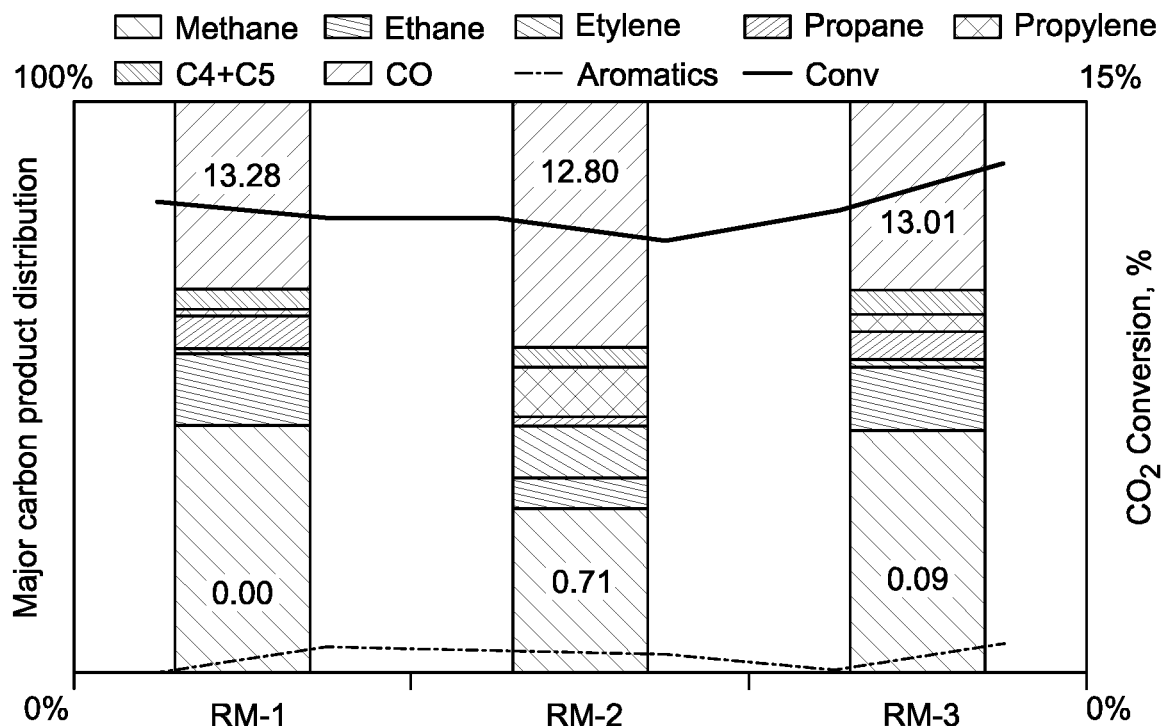
FIG. 8 is a bar graph depicting major carbon product distribution, and $CO_2$ conversion, for the red mud samples, according to certain embodiments.

The performance of the prepared catalysts was evaluated for $CO_2$ hydrogenation using a fixed-bed laboratory-scale reactor. The temperature of the catalyst bed was in the range of 300-400° C. and the hydrogen pressure was between 30-40 bar. The feed includes $CO_2$ and $H_2$ in a volumetric ratio of 1:3. The products were analyzed using an online-gas chromatograph (GC) equipped with multiple detectors. Results are shown here in Table 4 and are graphically represented in FIG. 8.

TABLE 4

Catalytic performance data of the red mud samples for $CO_2$ hydrogenation

| Product Composition (wt. %) | RM-1 | RM-2 | RM-3 |
|---|---|---|---|
| Methane | 43.63 | 28.80 | 42.54 |
| Ethane | 12.55 | 5.40 | 11.28 |
| Ethylene | 0.88 | 8.79 | 1.37 |
| Propane | 5.78 | 1.74 | 4.87 |
| Propylene | 1.27 | 8.65 | 2.87 |
| $C_4 + C_5$ | 3.44 | 3.51 | 4.24 |
| Aromatics | 0.00 | 0.71 | 0.09 |

TABLE 4-continued

Catalytic performance data of the red mud samples for $CO_2$ hydrogenation

| Product Composition (wt. %) | RM-1 | RM-2 | RM-3 |
|---|---|---|---|
| Carbon monoxide | 32.45 | 42.39 | 32.72 |
| Conversion | 13.28 | 12.80 | 13.01 |

Table 4 shows that RM-1 showed 13.28% $CO_2$ conversion, whereas RM-2 and RM-3 showed 12.80 and 13.01% $CO_2$ conversion, respectively. CO is a significant product in RM-2, whereas methane is the major product in the case of RM-1 and RM-3. A significant amount of ethylene and propylene and traces of aromatics are also produced over RM-2. The higher iron content and the suitable surface area values may have helped RM-2 to produce higher olefins even though the $CO_2$ conversion values are slightly lesser than RM-1.

Example 5: Performance Testing of the Red Mud-Based Catalysts

Figure 9:
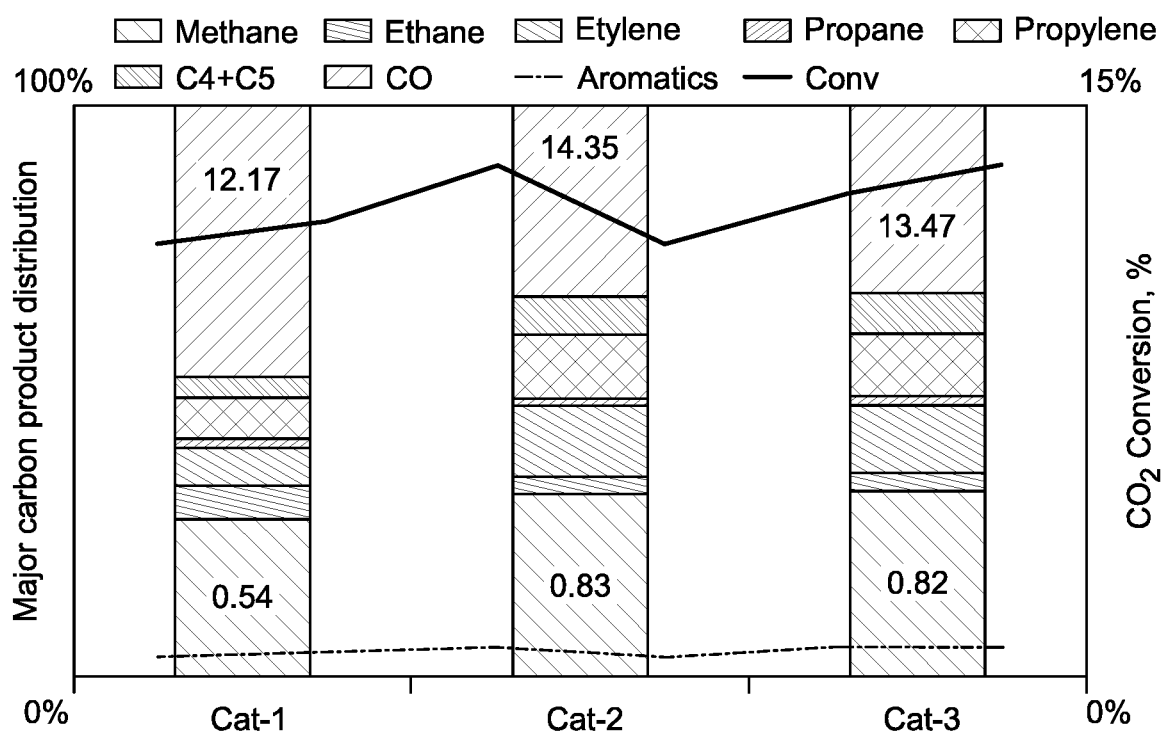
FIG. 9 is a bar graph depicting the major carbon product distribution, and $CO_2$ conversion, for red mud-based catalysts, prepared for $CO_2$ hydrogenation, according to certain embodiments.

The performance of modified red mud-based catalysts was evaluated for $CO_2$ hydrogenation in the same method as described in Example 4. Cat-1 showed 12.17% $CO_2$ conversion, whereas Cat-2 and Cat-3 showed 13.47 and 14.35% $CO_2$ conversion, respectively, as shown in Table 5 and FIG. 9.

TABLE 5

Catalytic performance data of the red mud-based catalysts for $CO_2$ hydrogenation

| Product Composition (wt. %) | Cat-1 | Cat-2 | Cat-3 |
|---|---|---|---|
| Methane | 27.51 | 31.88 | 32.28 |
| Ethane | 5.77 | 2.92 | 3.19 |
| Ethylene | 6.71 | 12.31 | 11.62 |
| Propane | 1.61 | 1.32 | 1.62 |
| Propylene | 7.17 | 11.18 | 10.95 |
| $C_4 + C_5$ | 3.60 | 0.09 | 0.11 |
| Aromatics | 0.54 | 0.83 | 0.82 |
| Carbon monoxide | 47.09 | 33.02 | 32.49 |
| Conversion | 12.17 | 13.47 | 14.35 |

CO is a significant product in Cat-1, whereas methane is produced in equal amounts in Cat-2 and Cat-3. Ethylene and propylene formation over Cat-2 and Cat-3 improved as compared to RM-2 and RM-3. In the case of RM-3, although the surface area value of RM-3 is higher, the lower iron content (4.98%) may have led to much lower olefin production. Upon modifying with the K promoter, RM-3 samples showed significant improvement in olefin formation, which is reflected in its affinity towards $NH_3$ and $CO_2$. Acidity values were reduced, and basicity values increased, leading to enhanced $CO_2$ adsorption and further RM-3 reaction with $H_2$ to produce desired products.

Aromatics formation is also enhanced over Cat-2 and Cat-3 as compared to RM-2 and RM-3, respectively. Aromatics production is marginal in quantity, a high-value commodity is produced over a cheap catalyst using $CO_2$, which is one of the environmentally harmful gases which needs immediate solutions for effective utilization.

Numerous modifications and variations of the present disclosure are possible in light of the above teachings. It is therefore to be understood that within the scope of the appended claims, the invention may be practiced otherwise than as specifically described herein.

The invention claimed is:

1. A carbon dioxide ($CO_2$) reduction method, comprising:
pulverizing and calcining a red mud catalyst composition at a temperature of at least 700° C. to form a calcined red mud catalyst composition, wherein the red mud catalyst composition comprises 7.89 to 18.77 wt. % Al, 4.98 to 23.88 wt. % Fe, 0.07 to 0.18 wt. % Mg, 4.47 to 7.66 wt. % Na, 0.05 to 0.19 wt. % P, 0.49 to 3.86 wt. % Ti, 0.05 to 0.16 wt. % V, 0.98 to about 2.57 wt. % C, 0.12 to 0.16 wt. % S, and less than 0.01 wt. % Mn, each wt. % based on a total weight of the red mud catalyst composition by inductively coupled plasma optical emission spectroscopy (ICP-OES),
wherein the red mud catalyst composition comprises particles having a specific surface area in a range of 16.6 to 58.0 square meter per gram ($m^2/g$) and a cumulative specific pore volume in a range of 0.035 to 0.067 cubic centimeter per gram ($cm^3/g$);
soaking and mixing particles of the pulverized and calcined red mud catalyst composition in a salt solution having a concentration of 0.5 to 10 wt. % KF based on a total weight of the salt solution, to form a reaction composition comprising a modified red mud catalyst composition; and
separating the modified red mud catalyst composition from the reaction composition and drying the separated modified red mud catalyst composition to obtain the modified red mud catalyst composition:
introducing a gaseous mixture of $CO_2$ and $H_2$ into a reactor containing particles of the modified red mud catalyst composition; and
reacting at least a portion of the $CO_2$ and $H_2$ in the gaseous mixture in the presence of the modified red mud catalyst composition at a temperature of 200 to 800° C., and under a pressure ranging from 5 to 100 bar to form a gaseous product comprising a chemical reduction product of the $CO_2$;
wherein a volume ratio of the $CO_2$ to the $H_2$ in the gaseous mixture is in a range of 1:10 to 10:1; and
wherein the gaseous product comprises an amount of 9% to 15% of ethylene, 9% to 13% of propylene, and 0.5% to 1.1% of aromatics, based on the total weight of the gaseous product.

2. The method of claim 1, wherein the reactor is at least one selected from the group consisting of a fixed-bed reactor, a trickle-bed reactor, a moving bed reactor, a rotating bed reactor, a fluidized bed reactor, and a slurry reactor.

3. The method of claim 1, wherein the reactor is a fixed-bed reactor in the form of a cylindrical reactor comprising:
a top portion;
a cylindrical body portion;
a bottom portion;
a housing having an open top and open bottom supportably maintained with the cylindrical body portion;
wherein the modified red mud catalyst composition is supportably retained within the housing permitting fluid flow therethrough;
at least one propeller agitator is disposed in the bottom portion of the reactor;
wherein the bottom portion is cone shaped or pyramidal; and
wherein a plurality of recirculation tubes fluidly connects the bottom portion of the cylindrical reactor with the cylindrical body portion of the cylindrical reactor.

4. The method of claim 1, wherein the volume ratio of the $CO_2$ to the $H_2$ is in a range of 1:1 to 1:5.

5. The method of claim 1, wherein the reacting is performed at a temperature of 300 to 400° C.

6. The method of claim 1, wherein the reacting is performed under a pressure ranging from 30 to 40 bar.

7. The method of claim 1, wherein the reacting chemically reduces 10 to 25% of the $CO_2$ based on a total weight of the gaseous mixture.

8. The method of claim 1, wherein the red mud catalyst composition is a waste product from an aluminum extraction process.

9. The method of claim 1, wherein the red mud catalyst composition has a hydrogen temperature-programmed reduction ($H_2$-TPR) of 0.5 to 5 millimoles per gram (mmol/g).

10. The method of claim 1, wherein the red mud catalyst composition has:

a temperature-programmed desorption of ammonia ($NH_3$-TPD) of 0.001 to 0.1 mmol/g;

a temperature-programmed desorption of carbon dioxide ($CO_2$-TPD) of 0.01 to 0.5 mmol/g.

11. The method of claim 1, wherein the gaseous product comprises methane, ethane, ethylene, propane, propylene, carbon monoxide, a C4-C9 hydrocarbon, and aromatics, wherein the C4-C9 hydrocarbon comprises butane, butene, butyne, pentane, pentene, pentyne, hexane, hexene, hexyne, cyclohexane, cyclohexene, heptane, heptene, heptyne, octane, octene, octyne, nonane, nonene, nonyne, their isomers, or mixtures thereof.

12. The method of claim 11, wherein the methane is present in the gaseous product at a concentration of 20 to 50 wt. %, and the carbon monoxide is present in the gaseous product at a concentration of 25 to 50 wt. %, each wt. % based on a total weight of the gaseous product.

* * * * *